US008524230B2

(12) United States Patent
Cua et al.

(10) Patent No.: US 8,524,230 B2
(45) Date of Patent: Sep. 3, 2013

(54) USE OF IL-23 AND IL-17 ANTAGONISTS TO TREAT AUTOIMMUNE OCULAR INFLAMMATORY DISEASE

(75) Inventors: Daniel J. Cua, Boulder Creek, CA (US); Robert A. Kastelein, Portola Valley, CA (US); Van T. Tsai, San Diego, CA (US); Rachel Caspi, Bethesda, MD (US); Phyllis Silver, Silver Spring, MD (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 23 days.

(21) Appl. No.: 12/643,152

(22) Filed: Dec. 21, 2009

(65) Prior Publication Data
US 2010/0111950 A1 May 6, 2010

Related U.S. Application Data

(62) Division of application No. 11/512,622, filed on Aug. 30, 2006, now abandoned.

(60) Provisional application No. 60/713,792, filed on Sep. 1, 2005, provisional application No. 60/837,312, filed on Aug. 11, 2006.

(51) Int. Cl.
*C07K 16/244* (2006.01)
*A61P 29/00* (2006.01)
*C07K 2316/96* (2006.01)
*A61K 39/395* (2006.01)

(52) U.S. Cl.
USPC ........... 424/133.1; 424/141.1; 424/142.1; 424/145.1; 514/20.8; 530/388.1; 530/388.15

(58) Field of Classification Search
None
See application file for complete search history.

(56) References Cited

U.S. PATENT DOCUMENTS

| | | | |
|---|---|---|---|
| 6,680,057 B1 | 1/2004 | Yao et al. | |
| 7,491,391 B2 * | 2/2009 | Benson et al. | 424/139.1 |
| 2004/0156849 A1 | 8/2004 | Gurney | |
| 2004/0219150 A1 | 11/2004 | Cua et al. | |
| 2005/0244874 A1 | 11/2005 | Kastelein et al. | |
| 2005/0287593 A1 | 12/2005 | Kastelein et al. | |
| 2006/0110429 A1 | 5/2006 | Reiff et al. | |
| 2006/0135518 A1 | 6/2006 | Wada et al. | |
| 2007/0009526 A1 | 1/2007 | Benson et al. | |

FOREIGN PATENT DOCUMENTS

| | | |
|---|---|---|
| WO | WO02/08285 | 1/2002 |
| WO | WO02/097048 | 12/2002 |
| WO | WO2004/042009 | 5/2004 |
| WO | WO2004/081190 | 9/2004 |
| WO | WO2004/101750 | 11/2004 |
| WO | WO 2004/101750 | * 11/2004 |
| WO | WO2005/010044 | 2/2005 |
| WO | WO2005/069933 | 8/2005 |
| WO | WO2006/013107 | 2/2006 |
| WO | WO 2006/013107 | * 2/2006 |
| WO | WO2006/036745 | 4/2006 |
| WO | WO2006/057859 | 6/2006 |
| WO | WO2006/069036 | 6/2006 |
| WO | WO2006/088833 | 8/2006 |
| WO | WO2007/005608 | 1/2007 |
| WO | WO2007/027714 | 3/2007 |
| WO | WO2007/076524 | 7/2007 |

OTHER PUBLICATIONS

Phillips, A., J Pharm Pharmacology, 2001, vol. 53, pp. 1169-1174.*
Vidal et al. European Journal of Cancer, 2005, vol. 41, pp. 2812-2818.*
Pirollo et al. Cancer Res, 2008, vol. 68, No. 5, pp. 1247-1250.*
Whitely et al, http://www.revoptom.com/continuing_education/tabviewtest/lessonid/107773/, 2011.*
U.S. Appl. No. 60/630,751, filed Nov. 24, 2004, Hampton et al.
U.S. Appl. No. 60/754,889, filed Dec. 29, 2005, Benson et al.
U.S. Appl. No. 60/815,828, filed Jun. 23, 2006, Dufner et al.
U.S. Appl. No. 60/695,679, filed Jun. 30, 2005, Lacy et al.
U.S. Appl. No. 60/637,819, filed Dec. 21, 2004, Giles-Komar et al.
U.S. Appl. No. 60/713,585, filed Aug. 31, 2005, Presta et al.
Alcon Research, Ltd., Notice of Opposition to EP1933869, Jul. 2010.
Becher, Burkhard, et al.; "Experimental autoimmune encephalitis and inflammation in the absence of interleukin-12"; *The Journal of Clinical Investigation*; 110(4):493-497 (2002), submitted by Opponent in opposition against EP1933869.
Bowman, Edward P., et al.; "Rationale and safety of anti-interleukin-23 and anti-interleukin-17A therapy", *Current Opinion in Infectious Disease*, 19:245-252 (2006.
Caspi, Rachel R., et al.; "Endogenous Systemic IFN-γ Has a Protective Role Against Ocular Autoimmunity in Mice", *Journal of Immunology*, 152:890-899 (1994).
Caspi, Rachel R., "Short Analytical Review IL-12 in Autoimmunity", *Clinical Immunology and Immunopathology*, 88(1):4-13 (1998).
Caspi, Rachel R.; "TH1 and TH2 Responses in Pathogenesis and Regulation of Experimental Autoimmune Uveoretinitis", *Intern. Rev. Immunology*, 21:197-208 (2002).
Caspi, Rachel R.; "Animal models of autoimmune and immune-mediated uveitis"; *Drug Discovery Today*; 3(1):3-9 (2006), submitted by Opponent in opposition against EP1933869.
Caspi, Rachel R.; "Mechanisms Underlying Autoimmune Uveitis", *Drug Discovery Today: Disease Mechanisms*, 3(2):199-206 (2006).
Centocor Ortho Biotech, Inc., Notice of Opposition to EP1933869, Jul. 2010.
Chapman, Andrew P.; "PEGylated antibodies and antibody fragments for improved therapy: a review"; *Advanced Drug Delivery Reviews*; 54(4):531-545 (2002), submitted by Opponent in opposition against EP1933869.
Chen, Yi, et al.; "Anti-IL-23 therapy inhibits multiple inflammatory pathways and ameliorates autoimmune encephalomyelitis", *The Journal of Clinical Investigations*, 116(5):1317-1326 (2006), submitted by Opponent in opposition against EP1933869.

(Continued)

*Primary Examiner* — Bridget E Bunner
*Assistant Examiner* — Fozia Hamud

(57) ABSTRACT

Novel methods and drug products for treating autoimmune ocular inflammatory disease are disclosed, which involve administration of agents that antagonize one or both of IL-17 and IL-23 activity.

1 Claim, No Drawings

(56) References Cited

OTHER PUBLICATIONS

Cua, Daniel J., Declaration, submitted by Schering Corporation to the European Patent Office in Feb. 28, 2011 in reply to oppositions against EP1933869.

Cua, Daniel J., et al.; "Interleukin-23 rather than interleukin-12 is the critical cytokine for autoimmune inflammation of the brain"; Nature; 421:744-748 (2009), submitted by Opponent in opposition against EP1933869.

Daniel, Carolin, et al.; "Immune Modulatory Treatment of Trinitrobenzene Sulfonic Acid Colitis with Calcitriol is Associated with a Change of a T Helper (Th) 1/Th17 to a Th2 and Regulatory T Cell Profile"; The Journal of Pharmacology and Experimental Therapeutics; 294(1):23-33 (2008), submitted by Opponent in opposition against EP1933869.

Dick, Andrew D., et al.; "Immunomodulation of autoimmune responses with monoclonal antibodies and immunoadhesins: treatment of ocular inflammatory disease in the next millennium"; Br. J. Ophthalmol.; 83:1230-1234 (1999), submitted by Opponent in opposition against EP1933869.

Fischer, Laurin G.; "The ocular manifestations of multiple sclerosis"; Journal of the American Optometric Association; 48(12):1511-1515 (1977), submitted by Opponent in opposition against EP1933869.

Gocho, Kiyoko, et al.; "Identification of Autoreactive T Cells in Vogt-Koyanagi-Harada Disease", Investigative Ophthalmology & Visual Science, 42(9):2004-2009 (Aug. 2001).

Gronvold Olsen, Erling, et al.; "The effect of steroids on the healing of the corneal endothelium"; ACTA Ophthalmologica; 82:893-899 (1984), submitted by Opponent in opposition against EP1933869.

Guidera, Ann C., et al.; "Keratitis, Ulceration, and Perforation Associated with Topical Nonsteroidal Anti-Inflammatory Drugs", American Academy of Ophthalmology, 108(5):936-944 (2001), submitted by Opponent in opposition against EP1933869.

Harrington, Laurie E., et al.; "Expanding the Effector CD4 T-cell repertoire: the Th17 lineage"; Current Opinion in Immunology; 18:349-356 (2006), submitted by Opponent in opposition against EP1933869.

International Search Report, International Application No. PCT/US2006/033840, Date of Mailing Feb. 16, 2007.

Iwakura, Yoichiro, et al.; "Teh IL-23/IL-17 axis in inflammation"; The Journal of Clinical Investigation; 116(5):1218-1222, submitted by Opponent in opposition against EP1933869, May 2006.

Jones, Leslie S., et al.; "IFN-γ-Deficient Mice Develop Experimental Autoimmune Uveitis in the Context of a Deviant Effector Response", Journal of Immunology, 158:5997-6005 (1997).

Kasche, Dr. Andre, Notice of Opposition to EP1933869, Oct. 2009.

Kobayashi, Michiko, et al.; "Identification and purification of natural killer cell stimulatory factor (NKSF), a cytokine with multiple biologic effects on human lymphocytes"; J. Exp. Med; 170:827-845 (1989), submitted by Opponent in opposition against EP1933869.

Kolls, Jay K., et at ; "Interleukin-17 Family Members and Inflammation", Immunity, 21:467-476 (Oct. 2004), submitted by Opponent in opposition against EP1933869.

Kulkarni, Prasad; "Review: Uveitis and Immunosuppressive Drugs", Journal of Ocular Pharmacology and Therapeutics, 17(2):181-187 (2001), submitted by Opponent in opposition against EP1933869.

Langrish, Claire L., et al.; "IL-12 and IL-23: Master Regulators of Innate and Adaptive Immunity", Immunological Reviews, 2004, 202:96-105 (2004), submitted by Opponent in opposition against EP1933869.

Langrish, Claire L., et al.; "IL-23 Drives a Pathogenic T Cell Population that Induces Autoimmune Inflammation", The Journal of Experimental Medicine, 201(2):233-240 (Jan. 17, 2005), submitted by Opponent in opposition against EP1933869.

Leonard, J. P., et al.; "Prevention of experimental autoimmune encephalomyelitis by antibodies against interleukin 12"; J. Exp. Med.; 181:381-386 (1995), submitted by Opponent in opposition against EP1933869.

Luger, Dror, et al; "Development of experimental autoimmune uveitis requires IL-23 but not the IL-17 producing T cell effector"; Immunology; S158:97.7 (2006), submitted by Opponent in opposition against EP1933869.

Maertzdorf, Jeroen, et al.; "IL-17 Expression in Human Herpetic Stromal Keratitis: Modulatory Effects on Chemokine Production by Corneal Fibroblasts"; The Journal of Immunology; 169:5897-5903 (2002), submitted by Opponent in opposition against EP1933869.

Mangan, Paul R., et al.; "Transforming growth factor-β induces development of the $T_H17$ lineage"; Nature; 441:231-234 (2006), submitted by Opponent in opposition against EP1933869.

McKenzie, Brent S., et al.; "Understanding the IL-23-IL-17 Immune Pathway", Trends in Immunology, 27(1):17-23 (Jan. 2006), submitted by Opponent in opposition against EP1933869.

Murphy, Craig A., et al; "Divergent Pro- and Antiinflammatoty Roles for IL-23 and IL-12 in Joint Autoimmune Inflammation"; J. Exp. Med.; 198(12):1951-1957 (2003), submitted by Opponent in opposition against EP1933869.

Nakajima, Hideto, et al.; "Monocyte chemoattractant protein-1 enhances HSV-induced encephalomyelitis by stimulating Th2 responses"; Journal of Leukocyte Biology; 70:374-380 (2001), submitted by Opponent in opposition against EP1933869.

Novarits AG, Notice of Opposition to EP1933869, Jul. 2010.

Ogawa, Atsuhiro, et al; "Neutralization of interleukin-17 aggravates dextran sulfate sodium-induced colitis in mice"; Clinical Immunology; 110:55-62 (2004), submitted by Opponent in opposition against EP1933869.

Pennesi, Giuseppina, et al.; "A Humanized Model of Experimental Autoimmunie Uveitis in HLA Class II Transgenic Mice", The Journal of Clinical Investigation, 111(8):1171-1180 (Apr. 2003).

Phillips, Anthony, J.; "The challenge of gene therapy and DNA delivery"; J. Pharm. and Pharmacology, 2001. vol. 53, pp. 1169-1174.

Pirollo, Kathleen F., et al., Targeted Delivery of small Interfering RNA: Approaching Effective Cancer Therapies:; Cancer Res. 2008, vol. 68(5), pp. 1247-1250.

Rakoff-Nahoum et al. and Uhlig et al.; "The Many Roads to Inflammatory Bowel Diseases", Immunity; 25(2):189-191 (2006).

Sartani, Gil, et al.; "Anti-Tumor necrosis factor alpha therapy suppresses the induction of experimental autoimmune uveoretinitis in mice by inhibiting antigen priming"; Investigatie Ophthalmology & Visual Science; 37(11):2211-2218 (1996), submitted by Opponent in opposition against EP1933869.

Smith, Justine R., et al.; "Differential efficacy of tumor necrosis factor inhibition in the management of inflammatory eye disease and associated rheumatic disease"; Arthritis Care & Research; 45:252-257 (2001), submitted by Opponent in opposition against EP1933869.

Stabler, Thomas, et al.; "Serum cytokine profiles in relapsing polychondritis suggest monocyte/macrophase activation"; Arthritis & Rheumatism; 50(11):3663-3667 (2004), submitted by Opponent in opposition against EP1933869.

Stanford, M., et al.; "Oral tolerization with peptide 336-351 linked to cholera toxin B subunit in preventing relapses of uveitis in Behcet's disease"; Clin. Exp. Immunol.; 137:201-208 (2004), submitted by Opponent in opposition against EP1933869.

Sugita, Sunao, et al.; "Melanocyte Lysis by Cytotoxic T Lymphocytes Recognizing the MART-1 Melanoma Antigen in HLA-A2 Patients with Vogt-Koyanagi-Harada Disease", International Immunology, 8(5):799-803 (1996).

Tarrant, Teresa K., et al.; "Endogenous IL-12 is Required for Induction and Expression of Experimental Autoimmune Uveitis", The Journal of Immunology, 161:122-127 (1998).

Tarrant, Teresa K., et al.; "Interleukin 12 Protects from a T Helper Type 1-Mediated Autoimmune Disease, Experimental Autoimmune Uveitis, through a Mechanism Involving Interferon γ, Nitric Oxide, and Apoptosis", Journal of Experimental Medicine, 189(2):219-230 (1999).

Toy, Dean, et al.; "Cutting Edge: Interleukin 17 Signals through a Heteromeric Receptor Complex", Journal of Immunology, 177(1):36-39 (2006).

Uveitis; www.en.wikipedia.org/wiki/uveitis; 4 pages (Apr. 2010), submitted by Opponent in opposition against EP1933869.

Veldhoen, Marc, et al.; "TGFβ in the context of an inflammatory cytokine milieu supports de novo differentiation of IL-17-producing T cells"; *Immunity*; 24:179-189 (2006), submitted by Opponent in opposition against EP1933869.

Vidal, Laura, et al., "Making Sense of Antisense"; *European Journal of Cancer*, 2005, vol. 41, pp. 2812-2818.

Xu, Hui, et al.; "Uveitogenicity is Associated with a Th1-like Lymphokine Profile: Cytokine-Dependent Modulation of Early and Committed Effector T Cells in Experimental Autoimmune Uveitis", *Cellular Immunology*, 178:69-78 (1997).

Xu, M., et al.; "Role of IL-12 in regulating herpes simplex keratitis (HSK)"; *Investigative Ophthalmology and Visual Science*; 43:p. E-Abstract 4306 (2002), submitted by Opponent in opposition against EP1933869.

Yamaki, Kunihiko, et al.; "Tyrosinase Family Proteins Are Antigens Specific to Vogt-Koyanagi-Harada Disease", *Journal of Immunology*, 165:7323-7329 (2000).

Yang, K., et al.; "Inhibitory effect of rapamycin and dexamethasone on production of IL-17 and IFN-γ in Vogt-Koyanangi-Harada patients"; *Br. J. Ophthalmol.*; 93:249-253 (2009), submitted by Opponent in opposition against EP1933869.

Yen, David, et al.; "IL-23 is essential for T cell-mediated colitis and promotes inflammation via IL-17 and IL-6", *The Journal of Clinical Investigation*, 116(5):1310-1316 (2006), submitted by Opponent in opposition against EP1933869.

Schering Corporation, reply of the patent proprietor to the notice(s) of opposition against EP1933869, Oct. 2009.

European Patent Office, Information about the result of oral proceedings for Opposition to EP1933869, Oct. 25, 2012.

\* cited by examiner

USE OF IL-23 AND IL-17 ANTAGONISTS TO TREAT AUTOIMMUNE OCULAR INFLAMMATORY DISEASE

The present application is a divisional of Ser. No. 11/512,622, filed Aug. 30, 2006 which claims benefit of U.S. provisional application No. 60/713,792, filed Sep. 1, 2005 and U.S. provisional application No. 60/837,312, filed Aug. 11, 2006.

STATEMENT REGARDING FEDERALLY SPONSORED RESEARCH AND DEVELOPMENT

This invention was made in part with Government support under Cooperative Research and Development Agreement (CRADA) Number M-01969-04, and amendments thereto, executed between Schering-Plough Biophamia and the National Eye Institute, National Institutes of Health. The Government of the United States of America has certain rights in this invention.

FIELD OF THE INVENTION

The present invention relates generally to the modulation of immune responses in the eye. More specifically, the invention relates to the use of antagonists of interleukin-23 (IL-23) and interleukin-17 (IL-17) to treat autoimmune ocular inflammatory disease.

BACKGROUND OF THE INVENTION

Ocular inflammatory disease (OID) is a general term embracing a number of diseases and conditions in which inflammation affects the eye or surrounding tissues. The diagnostic name given to an OID is typically based on the location of the ocular inflammation. For example, uveitis is inflammation in the uveal tract; scleritis is inflammation of the sclera, pars planitis is inflammation of the pars plana, and so forth. OIDs cause pain, irritation, and watering, and may result in loss of visual function. For example, uveitis is the third leading cause of blindness in the developed world. OIDs can be caused by infections, malignancy, exposure to toxins, response to surgery or injury, and autoimmune disorders.

A number of autoimmune diseases exist in which the eye or various parts of the eye becomes a target for an immune-mediated inflammatory attack. Patients with an autoimmune-mediated OID (AOID) often exhibit cellular and humoral responses to retinal antigens such as retinal arrestin (retinal soluble antigen, S—Ag), interphotoreceptor retinoid binding protein (IRB), and antigens related to melanin and its metabolism, including GP100, MART1, TRP1 and TRP2 (Pennesi, G. et al. (2003) *J. Clin. Invest.* 111:1171-1180; Gocho, K. et al. (2001) *Invest. Ophthalmol. Vis. Sci.* 42:2004-2009; Sugita S. et al., (1996) *Int. Immunol.* 8:799-803; Yamake, K. et al. (2000) *J. Immunol.* 165:7323-7329. However, in many cases of AOID, the target antigen(s) are not known.

Often, OID is a manifestation of a systemic autoimmune disease, and the eye is one of a variety of organs throughout the body that are being attacked. Examples of such systemic autoimmune diseases include rheumatoid arthritis, systemic lupus erythematosus, polyarteritis nodosa, relapsing polychondritis, Wegener's granulomatosis, scleredemia, Behcet's disease, Reiter's disease, inflammatory bowel disease (ulcerative colitis and Crohn's disease) and ankylosing spondylitis. However, the eye may be the specific and only target affected in autoimmune diseases such as ocular cicatricial pemphigoid, Mooren's corneal ulcer, and various forms of uveitis.

AOIDs such as uveitis have been treated by various classes of compounds including steroids and nonsteroidal anti-inflammatory agents such as dexamethasone, fluorometholone, prednisolone, indomethacin, aspirin, flubiprofen and diclofenac. However, a number of uveitis cases are not responsive to or become refractory to these drugs (see, e.g., Kulkarni, P. (2001) *Journal of Ocular Pharmacology And Therapeutics* 17:181-187). Also, these drugs are associated with serious side effects such as cataracts, glaucoma, delayed wound healing, altered prostaglandin production, corneal complications, increased ocular pressure, superinfections, and reduced immunity to infection (see, e.g., Id., at 181; Guidera, A. C., et al. (2001) *Ophthalmology* 108:936-944; Olsen, E. G. & Davanger M. (1984) *Acta Ophtalmol.* 62:893-899).

Because the existing therapies for AOID have less than optimal efficacy or undesirable side effects, new treatment regimens are needed. It has been suggested that it may be clinically beneficial to modulate the immunoregulatory mechanisms involved in the pathogenesis of AOID (Caspi, R. R. (2002) *Int Rev Immunol* 21:197-208).

These pathogenic mechanisms have been investigated using experimental autoimmune uveitis (EAU), which is an animal model of human autoimmune uveitis. EAU is induced in experimental animals such as mouse, rat, guinea pig, rabbit, and monkey by immunization with a retinal antigen shown to be reactive in uveitis patients (e.g., arrestin, IRBP, rhodopsin/opsin, phosducin, recoverin) or by infusion of T cells specific for these antigens. Studies using the EAU model provided apparently contradictory evidence about the mechanisms for induction and progression of this disease. The results of some experiments indicated that the main pathogenic pathway in EAU was due to the role of interleukin-12 (IL-12) in promoting the generation of IFN-γ producing Th1 effector cells (Caspi, R. R. (2002) *Int Rev Immunol* 21:197-208; Tarrant, T. K. et al., (1998) *J. Immunol.* 161:122-127; Caspi, R. R. (1998) *Clin Immunol Immunopathol* 88:4-13; Xu, H. et al. (1997) *Cell Immunol* 178:69-78. However other experiments showed that IFN-γ deficient knock-out mice were susceptible for EAU, that EAU is exacerbated by neutralization of endogenous IFN-γ, and that elevated levels of IFN-γ were protective against EAU in wild-type mice (Caspi, R. R. et al. (1994) *J. Immunol.* 152:890-899; Jones et al., *J. Immunol.* 158:5997-6005; Tarrant, T. K., et al. (1999) *J. Exp. Med* 189:219-230.

Thus, prior to the present invention, it was not clear which immune pathways should be targeted in developing therapies for preventing or treating autoimmune ocular inflammatory disease.

SUMMARY OF THE INVENTION

The present invention is based on the discoveries that (1) blocking interleukin-2 (IL-23) or interleukin-17 (IL-17) activity prevents induction of EAU; (2) after induction, neutralization of IL-17 activity inhibits or reverses progression of EAU, but neutralization of IL-23 activity has little to no effect; and (3) IL-17 activity is not necessary for induction of EAU. The present invention uses IL-23 and/or IL-17 antagonists in methods and compositions for treating or preventing autoimmune ocular inflammatory disease. These antagonists antagonize either the target cytokine itself or a functional receptor for the target cytokine.

IL-23 is a heterodimeric cytokine comprised of two subunits: p19, which is unique to IL-23; and p40, which is shared with IL-12. IL-23 mediates signaling by binding to a heterodimeric receptor, comprised of IL-23R and IL-12Rbeta1

(IL12RB1), which is shared by the IL-12 receptor. A recent paper reported that IL-23 promotes a T cell population characterized by the production of IL-17, IL-17F, TNF, IL-6 and other factors, and named these cells "$Th_{17}$ cells" (Langrish et al. (2005) *J. Exp. Med.* 201:233-240)).

IL-17, which was originally named cytotoxic T-Lymphocyte-associated antigen 8 (CTLA8) is a homodimeric cytokine that binds to IL-17RA (also known as IL17R) and IL-17C. The functional receptor for IL-17 is believed to be a multimeric receptor complex comprising one or both of IL-17RA and IL-17RC (e.g., an IL-17RA homodimer, an IL-17RC homodimer, or an IL-17RA/IL-17RC heterodimer) and possibly a third, as yet unknown, protein (Toy, D. et al., (2006) *J. of Immunol.* 177(1):36-39; unpublished data).

In one aspect, the invention provides a method of treating a patient with an autoimmune ocular inflammatory disease, comprising administering to the patient an IL-17 antagonist. The presence of an AOID need not be directly diagnosed, but may be inferred by a diagnosis that the patient has an ocular inflammation that is of putative autoimmune etiology and/or that exhibits one or more characteristics of an autoimmune response. A particularly preferred AOID is autoimmune uveitis, e.g., uveitis without an infectious etiology.

The IL-17 antagonist may inhibit the expression of IL-17 or IL-17R or IL-17RC or may inhibit IL-17 signaling by directly or indirectly interacting with one or more of these polypeptides to prevent a functional ligand-receptor interaction. In some preferred embodiments, the IL-17 antagonist is an antibody or antibody fragment that binds to and inhibits the activity of either IL-17, IL17R or IL17C. In one particularly preferred embodiment, the IL-17 antagonist is a monoclonal antibody that specifically binds to IL-17. In other preferred embodiments, the IL-17 antagonist is a bispecific antibody that binds to and inhibits the activity of IL-23p19 and IL-17; IL-23p19 and IL-17RA; IL-23R and IL-17; or IL-23R and IL-17RA. In another particularly preferred embodiment, the IL-17 antagonist is a bispecific antibody that binds to and inhibits the activity of IL-23p19 and IL-17.

In some embodiments, the IL-17 antagonist is administered according to a specified treatment regimen. For example, in one embodiment, a specified dose of the antagonist is administered at a specified interval during a first treatment period, which may end after disappearance of one or more symptoms of the AOID, or within a specified period of time. In a preferred embodiment, the treatment regimen further comprises gradually reducing the dose of the IL-17 antagonist during a second treatment period that begins upon the end of the first treatment period and ends when therapy with the IL-17 antagonist is stopped. The duration of the second treatment period is typically between one and twelve months, one and nine months, one and six months, or one and three months.

In some preferred embodiments, the specified treatment regimen also comprises administration of an IL-23 antagonist to the patient during each of the first and second treatment periods, or during only the second treatment period. The IL-23 antagonist may inhibit the expression of either subunit of the cytokine (IL-23p19 or p40), either subunit of the functional receptor (IL-23R or IL-12beta1), or may inhibit IL-23 signaling by directly or indirectly interacting with one or more of these polypeptides to prevent a functional ligand-receptor interaction. In some preferred embodiments, the IL-23 antagonist is an antibody or antibody fragment that binds to and inhibits the activity of either IL-23p19 or IL-23R. In one particularly preferred embodiment, the IL-23 antagonist is a monoclonal antibody that specifically binds to IL-23p19.

The IL-23 antagonist may be administered at a specified dose at a specified interval during one or both of the first and second treatment periods. The dose of the IL-23 antagonist administered in the second treatment period may be lower than the dose administered in the first period. Also, in any or both of the treatment periods, the doses of the IL-17 and IL-23 antagonists may be the same or different from each other. Similarly, the two antagonists may be administered at the same or different intervals during each treatment period. During the second treatment period, the dose of the IL-17 antagonist may be reduced while the dose of the IL-23 antagonist is held constant, or the dose of each antagonist may be gradually reduced.

In other preferred embodiments, the dose of the IL-23 antagonist is held constant during the second treatment regimen and therapy with the IL-23 antagonist is continued during a third treatment period that begins upon the end of the second treatment period (i.e., when therapy with the IL-17 antagonist is stopped). During the third treatment period, the IL-23 antagonist may be administered at the same dose and interval as in the second treatment period or may be administered at a lower dose and/or less frequent interval than used in the previous period. The dose of the IL-23 antagonist may also be gradually reduced during the third treatment period. The duration of the third treatment period is typically between one and twelve months, one and nine months, one and six months, or one and three months.

In still other embodiments, the specified treatment regimen also comprises administering a therapeutic agent that does not antagonize IL-17 or IL-23 activity but is capable of alleviating at least one symptom of the AGED or at least one side effect of the IL-17 or IL-23 antagonists during any or all of the treatment periods. In some preferred embodiments, the therapeutic agent is a steroid or a nonsteroidal anti-inflammatory agent (e.g., NSAID) that is known to have efficacy in treating uveitis. In other preferred embodiments, the therapeutic agent targets a cytokine that promotes the Th1 response.

Another aspect of the invention provides a method of prophylactically treating a patient who is diagnosed as being susceptible for an autoimmune ocular inflammatory disease, which comprises administering to the patient an antagonist of one or both of IL-23 and IL-17. In some preferred embodiments of this prophylactic method, the susceptibility diagnosis is based on the patient having a previous incidence of ocular inflammation. In other preferred embodiments, the susceptibility diagnosis is based on the patient having a systemic autoimmune disease. The antagonist may be administered in a specified dose at a specified interval during a first treatment period, which typically ends after three months, six months, nine months or after two years of therapy with the antagonist. In some preferred embodiments, the dose of the antagonist is gradually reduced during a second treatment period that begins upon the end of the first treatment period, and typically has a duration of between one and three months.

In a still further aspect, the invention provides a method of treating a patient for an autoimmune ocular inflammatory disease, comprising administering to the patient an IL-23 antagonist. The IL-23 antagonist may be administered at a specified interval during a first treatment period, which is followed by a second treatment period in which the IL-23 antagonist is administered at a lower dose or at less frequent intervals, or at gradually reduced doses. Therapy with the Il-23 antagonist will typically continue for at least three to six months and may continue for as many as 12 months, 18 months or 24 months.

Another aspect of the invention is the use of an IL-17 antagonist or an IL-23 antagonist for the preparation of a pharmaceutical composition for the treatment or prevention of an autoimmune ocular inflammatory disease (AOID) in a patient. In preferred embodiments, the pharmaceutical composition is for administering the antagonist according to any of the treatment regimens described herein.

In a still further aspect, the invention provides a manufactured drug product for treating an autoimmune ocular inflammatory disease. The drug product comprises (i) a first pharmaceutical formulation comprising an IL-17 antagonist; and (ii) a second pharmaceutical formulation comprising an IL-23 antagonist. In preferred embodiments, the drug product includes product information which comprises instructions for administering the pharmaceutical formulations according to any of the treatment regimens described herein.

DETAILED DESCRIPTION

I. Definitions

So that the invention may be more readily understood, certain technical and scientific terms are specifically defined below. Unless specifically defined elsewhere in this document, all other technical and scientific terms used herein have the meaning that would be commonly understood by one of ordinary skill in the art to which this invention belongs when used in similar contexts as used herein.

As used herein, including the appended claims, the singular forms of words such as "a," "an," and "the," include their corresponding plural references unless the context clearly dictates otherwise.

"Antagonist" means any molecule that can prevent, neutralize, inhibit or reduce a targeted activity, i.e., the activity of a cytokine such as IL-17 or IL-23, either in vitro or in vivo. Cytokine antagonists include, but are not limited to, antagonistic antibodies, peptides, peptide-mimetics, polypeptides, and small molecules that bind to a cytokine (or any of its subunits) or its functional receptor (or any of its subunits) in a manner that interferes with cytokine signal transduction and downstream activity. Examples of peptide and polypeptide antagonists include truncated versions or fragments of the cytokine receptor (e.g., soluble extracellular domains) that bind to the cytokine in a manner that either reduces the amount of cytokine available to bind to its functional receptor or otherwise prevents the cytokine from binding to its functional receptor. Antagonists also include molecules that prevent expression of any subunit that comprises the cytokine or its receptor, such as, for example, antisense oligonucleotides which target mRNA, and interfering messenger RNA, (see, e.g., Arenz and Schepers (2003) *Naturwissenschaften* 90:345-359; Sazani and Kole (2003) *J. Clin. Invest.* 112:481-486; Pirollo, et al. (2003) *Pharmacol. Therapeutics* 99:55-77; Wang, et al. (2003) *Antisense Noel. Acid Drug Devel.* 13:169-189). The inhibitory effect of an antagonist can be measured by routine techniques. For example, to assess the inhibitory effect on cytokine-induced activity, human cells expressing a functional receptor for a cytokine are treated with the cytokine and the expression of genes known to be activated or inhibited by that cytokine is measured in the presence or absence of a potential antagonist. Antagonists useful in the present invention inhibit the targeted activity by at least 25%, preferably by at least 50%, more preferably by at least 75%, and most preferably by at least 90%, when compared to a suitable control.

"Antibody" refers to any form of antibody that exhibits the desired biological activity, such as inhibiting binding of a ligand to its receptor, or by inhibiting ligand-induced signaling of a receptor. Thus, "antibody" is used in the broadest sense and specifically covers, but is not limited to, monoclonal antibodies (including full length monoclonal antibodies), polyclonal antibodies, and multispecific antibodies (e.g., bispecific antibodies).

"Antibody fragment" and "antibody binding fragment" mean antigen-binding fragments and analogues of an antibody, typically including at least a portion of the antigen binding or variable regions (e.g. one or more CDRs) of the parental antibody. An antibody fragment retains at least some of the binding specificity of the parental antibody. Typically, an antibody fragment retains at least 10% of the parental binding activity when that activity is expressed on a molar basis. Preferably, an antibody fragment retains at least 20%, 50%, 70%, 80%, 90%, 95% or 100% or more of the parental antibody's binding affinity for the target. Examples of antibody fragments include, but are not limited to, Fab, Fab', F(ab')$_2$, and Fv fragments; diabodies; linear antibodies; single-chain antibody molecules, e.g., sc-Fv; and multispecific antibodies formed from antibody fragments. Engineered antibody variants are reviewed in Holliger and Hudson (2005) *Nat. Biotechnol.* 23:1126-1136.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the CH3 domains.

A "Fab' fragment" contains one light chain and a portion of one heavy chain that contains the $V_H$ domain and the $C_H1$ domain and also the region between the $C_H1$ and $C_H^2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody (or "scFv antibody") refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenberg and Moore eds. Springer-Verlag, New York, pp. 269-315. See also, International Patent Application Publication No. WO 88/01649 and U.S. Pat. Nos. 4,946,778 and 5,260,203.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448.

A "domain antibody fragment" is an immunologically functional immunoglobulin fragment containing only the variable region of a heavy chain or the variable region of a light chain. In some instances, two or more $V_H$ regions are covalently joined with a peptide linker to create a bivalent domain antibody fragment. The two $V_H$ regions of a bivalent domain antibody fragment may target the same or different antigens.

Autoimmune-mediated ocular inflammatory disease (AOID) means any disease or condition in which (a) inflammation is present in any part of the eye or surrounding tissues (including the optic nerve, blood vessels, muscles) and (b) the inflammation is part of an immune response that requires or is promoted by one or both of IL-23 and IL-17. Intraocular inflammation without an infectious etiology is typically considered an AOID. Nonlimiting examples of AOIDs are listed below.

Birdshot retinochoriodopathy (BSRC): A chronic intraocular inflammatory disease affecting mainly the back (posterior) part of the eye. BSRC is distinct from other forms of posterior uveitis that have a strong association with the HLA-A29.2 antigen. Its etiology remains unknown. An autoimmune mechanism is likely to play an important pathogenic role.

Ocular cicatricial pemphigoid (OCP): A systemic autoimmune disease. Mounting evidence supports the concept of immunoregulatory dysfunction: antibodies are directed against the basement membrane zone (BMZ) of the conjunctiva and other mucous membranes derived from stratified squamous epithelia and occasionally the skin. OCP is a vision threatening illness that usually requires treatment with immunosuppression.

Keratitis, peripheral ulcerative Keratitis: Keratitis is inflammation of the cornea, the outer, transparent, dome-like structure that forms the anterior most part of the outer coat of the eye. If ulcers develop in the peripheral cornea, it is referred to as peripheral ulcerative Keratitis.

"Sympathetic ophtahlmia" is an AOID in which a trauma to one eye precipitates at a later time a destructive inflammation in the other ("sympathizing") eye, apparently due to an autoimmune response to antigens released from the injured eye.

Vogt-Koyanagi Harada (VKH): Vogt-Koyanagi-Harada syndrome (VKH), formerly known as uveomenigitic syndrome is a systemic disorder involving multiple organ systems, including the ocular, auditory, nervous, and integumentary (skin) systems. Severe bilateral panuveitis associated with subretinal fluid accumulation is the hallmark of ocular VKH.

Fuchs' heterochromic iridocyclitis: A chronic, unilateral anterior uveitis characterized by iris heterochromia, a condition in which one eye is a different color from the other. The uveitis typically occurs in the lighter colored eye of a young adult.

"Binding compound" refers to a molecule, small molecule, macromolecule, antibody, a fragment or analogue thereof, or soluble receptor, capable of binding to a specified target. "Binding compound" also may refer to any of the following that are capable of binding to the specified target: a complex of molecules (e.g., a non-covalent molecular complex); an ionized molecule; and a covalently or non-covalently modified molecule (e.g., modified by phosphorylation, acylation, cross-linking, cyclization, or limited cleavage). In cases where the binding compound can be dissolved or suspended in solution, "binding" may be defined as an association of the binding compound with a target where the association results in reduction in the normal Brownian motion of the binding compound.

"Binding composition" refers to a binding compound in combination with at least one other substance, such as a stabilizer, excipient, salt, buffer, solvent, or additive.

"Bispecific antibody" means an antibody that has two antigen binding sites having specificities for two different epitopes, which may be on the same antigen, or on two different antigens. Bispecific antibodies include bispecific antibody fragments. See, e.g., Hollinger, et al. (1993) *Proc. Natl. Acad. Sci. USA*. 90: 6444-48, Gruber, et al., *J. Immunol.* 152: 5368 (1994).

"Consists essentially of" and variations such as "consist essentially of" or "consisting essentially of" as used throughout the specification and claims, indicate the inclusion of any recited elements or group of elements, and the optional inclusion of other elements, of similar or different nature than the recited elements, which do not materially change the basic or novel properties of the specified dosage regimen, method, or composition. As a nonlimiting example, a cytokine which consists essentially of a recited amino acid sequence may also include one or more amino acids that do not materially affect the properties of the cytokine.

"Interleukin-12R beta1" or "IL12RB1" means a single polypeptide chain consisting essentially of the sequence of the mature form of human IL12RB1 as described in NCBI Protein Sequence Database Accession Numbers NP714912, NP005526 or naturally occurring variants thereof.

"Interleukin, 17" (or "IL-17") means a protein consisting of one or two polypeptide chains, with each chain consisting essentially of the sequence of the mature form of human IL17A as described in any of NCBI Protein Sequence Database Accession Numbers NP002181, AAH67505, AAH67503, AAH67504, AAH66251, AAH66252 or naturally occurring variants thereof.

"IL-17R" or "IL-17RA" means a single polypeptide chain consisting essentially of the sequence of the mature form of human IL-17RA as described in WO 96/29408 or in any of NCBI Protein Sequence Database Accession Numbers: NP 055154, Q96F46, CAJ86450, or naturally occurring variants of these sequences.

"IL-17RC" means a single polypeptide chain consisting essentially of the sequence of the mature form of human IL-17RC as described in WO 238764A2 or in any of NCBI Protein Sequence Database Accession Numbers NP703191, NP703190 and NP116121, or naturally occurring variants of these sequences.

"Interleukin-23 (or "IL-23) means a protein consisting of two polypeptide chains. One chain consists essentially of the sequence of the mature form of human IL23, subunit p19 (also known as IL23A) as described in any of NCBI Protein Sequence Database Accession Numbers NP057668, AAH67511, AAH66267, AAH66268, AAH66269, AAH667512, AAH67513 or naturally occurring variants of these sequences. The other chain consists essentially of the sequence of the mature form in of human IL12, subunit p40 (also known as IL12B and IL23, subunit p40) as described in any of NCBI Protein Sequence Database Accession Numbers NP002178, P29460, AAG32620, AAH74723, AAH67502, AAH67499, AAH67498, AAH67501 or naturally occurring variants of these sequences.

"Interleukin-23R" or "IL-23R" means a single polypeptide chain consisting essentially of the sequence of the mature form of human IL23R as described in NCBI Protein Sequence Database Accession Number NP653302 or naturally occurring variants thereof.

"Monoclonal antibody" or "mAb" means an antibody obtained from a substantially homogeneous population of antibodies, and is not to be construed as requiring production of the antibody by any particular method.

"Parenteral administration" means an intravenous, subcutaneous, or intramuscular injection.

"Small molecule" means a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. Peptide mimetics of antibodies and cytokines are known in the art. See, e.g., Casset, et al. (2003) *Biochem. Biophys. Res. Commun.* 307: 198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al.

"Specific" or "specifically", when referring to the binding interaction between the members of a binding pair, such as a cytokine and its receptor, and antibody and its antigen or epitope, indicates a binding reaction which is determinative of the presence of one member of the binding pair in a heterogeneous population of proteins and other biologics. Thus, under designated conditions, one member of a binding pair has a significantly greater affinity for the other member of the binding pair than for irrelevant proteins. For example, an antibody is considered to be specific for a particular protein if it binds to that protein with an affinity that is at least 10-fold, and preferably 50-fold higher than its affinity for a different protein. An antibody that "specifically binds" to a protein comprising a particular epitope does not bind to any measurable degree to proteins that do not comprise that epitope. Preferably, an antibody that is specific for a target protein will have an affinity toward the target protein that is greater than about $10^9$ liters/mol, as determined, e.g., by Scatchard analysis (Munsen, et al. (1980) *Analyt. Biochem.* 107:220-239).

"Treat" or "Treating" means to administer a therapeutic agent, such as a composition containing any of the IL-17 and IL-23 antagonists described herein, internally or externally to a patient in need oldie therapeutic agent. Typically, the agent is administered in an amount effective to prevent or alleviate one or more disease symptoms, or one or more adverse effects of treatment with a different therapeutic agent, whether by preventing the development of, inducing the regression of, or inhibiting the progression of such symptom(s) or adverse effect(s) by any clinically measurable degree. The amount of a therapeutic agent that is effective to alleviate any particular disease symptom or adverse effect (also referred to as the "therapeutically effective amount") may vary according to factors such as the disease state, age, and weight of the patient, and the ability of the therapeutic agent to elicit a desired response in the patient. Whether a disease symptom or adverse effect has been alleviated can be assessed by any clinical measurement typically used by physicians or other skilled healthcare providers to assess the severity or progression status of that symptom or adverse effect. When a therapeutic agent is administered to a patient who has active disease, a therapeutically effective amount will typically result in a reduction of the measured symptom by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%. While an embodiment of the present invention (e.g., a treatment method or article of manufacture) may not be effective in preventing or alleviating the target disease symptom(s) or adverse effect(s) in every patient, it should alleviate such symptom(s) or effect(s) in a statistically significant number of patients as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

Uveitis means inflammation affecting one or more of the three parts of the eye that make up the uvea: the iris (the colored part of the eye), the ciliary body (behind the iris, responsible for manufacturing the fluid inside the eye) and the choroid (the vascular lining tissue underneath the retina). Panuveitis denotes the presence of inflammation in multiple parts of the same eye (anterior, intermediate, and posterior sections).

Uveitis can be either acute or chronic. The chronic form is more often associated with systemic disorders including ankylosing spondylitis, Behcet's syndrome, inflammatory bowel disease, juvenile rheumatoid arthritis, Reiter's syndrome, sarcoidosis, syphilis, tuberculosis, and Lyme disease.

Anterior uveitis, which involves inflammation in the front part of the eye, is the most common form of uveitis. The inflammation is usually isolated to the iris; thus, anterior uveitis is often called iritis. In some patients, anterior uveitis may be associated with the presence of an autoimmune disease such as rheumatoid arthritis or ankylosing spondylitis, but most cases of anterior uveitis occur in otherwise healthy people and do not indicate an underlying systemic disease. This OID may affect only one eye and is most common in young and middle-aged people. A history of an autoimmune disease is a risk factor. Most attacks of anterior uveitis last from a few days to weeks with treatment, but relapses are common.

Intermediate uveitis denotes an idiopathic inflammatory syndrome mainly involving the anterior vitreous, peripheral retina, and ciliary body, with minimal or no anterior segment or chorioretinal inflammatory signs.

Pars planitis is inflammation of the pars plana, a narrow area between the iris and the choroid. Pars planitis usually occurs in young men and is generally not associated with any other disease. However, there have been a few case reports of an association with Crohn's disease and some experts suggest a possible association with multiple sclerosis. For this reason, these experts recommend that patients over 25 years old diagnosed with pars planitis receive an MRI of their brain and spine.

Posterior uveitis affects the back portion of the uveal tract and involves primarily the choroid. This is called choroiditis. Posterior uveitis is characterized by inflammation of the layer of blood vessels underlying the retina, and usually of the retina as well. If the adjacent retina is also involved, the condition is typically called chorioretinitis. Posterior uveitis may follow a systemic infection or occur in association with an autoimmune disease. In posterior uveitis, the inflammation may last from months to years and may cause permanent vision damage, even with treatment.

II. General

The present invention provides methods of using antagonists of IL-17 and IL-23 activity to treat autoimmune ocular inflammatory disease.

IL17 activity, which is reviewed in Kolls, J. et al. (2004) *Immunity Vol.* 21, 467-476, includes promoting accumulation of neutrophils in a localized area and the activation of neutrophils. IL17 can induce or promote the production of any of the following proinflammatory and neutrophil-mobilizing cytokines, depending on the cell type: IL-6, MCP-1, CXCL8 (IL-8), CXCL1, CXCL6, TNFα, IL-1β, G-CSF, GM-CSF, MMP-1, and MMP-13.

IL-23 activity includes inducing the proliferation of memory T cells, PHA blasts, CD45RO T cells, CD45RO T cells; and enhance production of interferon-gamma (IFNγ) by PHA blasts or CD45RO T cells. In contrast to IL-12, IL-23 preferentially stimulates memory as opposed to naïve T cell populations in both human and mouse. IL-23 activates a number of intracellular cell-signaling molecules, e.g., Jak2, Tyk2, Stat1, Stat2, Stat3, and Stat4. IL-12 activates this same group of molecules, but Stat4 response to IL-23 is relatively weak, while Stat4 response to IL-12 is strong (Oppmann, et al., supra; Parham, et al. (2002) *J. Immunol.* 168:5699-5708). IL-23 has also been implicated in the maintenance and proliferation of IL-17 producing cells, also known as Th$_{17}$ cells (see, Cua and Kastelein (2006) *Nature Immunology* 7:557-559).

Antagonists useful in the present invention include a soluble receptor comprising the extracellular domain of a functional receptor for IL-17 or IL-23. Soluble receptors can be prepared and used according to standard methods (see, e.g., Jones, et al. (2002) *Biochim. Biophys. Acta* 1592:251-263; Prudhomme, et al. (2001) *Expert Opinion Biol. Ther.* 1:359-373; Fernandez-Botran (1999) *Crit. Rev. Clin. Lab Sci.* 36:165-224).

Preferred IL-17 antagonists for use in the present invention are antibodies that specifically bind to, and inhibit the activity of, any of IL-17, IL-17RA, IL-17RC, and a heteromeric complex comprising IL-17RA and IL-17RC. More preferably, the target of the IL-17 antagonist is IL-17 or IL-17RA. Particularly preferred IL-17 antagonists specifically bind to, and inhibit the activity of IL-17.

Another preferred IL-17 antagonist for use in the present invention is a bispecific antibody, or bispecific antibody fragment, which also antagonizes IL-23 activity. Such bispecific antagonists specifically bind to, and inhibits the activity of, each member in any of the following combinations: IL-17 and IL-23; IL-17 and IL-23p19; IL-17 and IL-12p40; IL-17 and an IL-23R/IL12RB1 complex; IL-17 and IL-23R; IL-17 and IL12RB1; IL17RA and IL-23; IL-17RA and IL-23p19; IL-17RA and IL-12p40; IL-17RA and an IL-23R/IL12RB1 complex; IL-17RA and IL-23R; IL-17RA and IL12RB1; IL17RC and IL-23; IL-17RC and IL-23p19; IL-17RC and IL-12p40; IL-17RC and an IL-23R/IL12RB1 complex; IL-17RC and IL-23R; IL-17RC and IL12RB1; an IL-17RA/IL-17RC complex and IL-23; an IL-17RA/IL-17RC complex and IL-23p19; an IL-17RA/IL-17RC complex and IL-12p40; an IL-17RA/IL-17RC complex and an IL-23R/IL12RB1 complex; an IL-17RA/IL-7RC complex and IL-23R; and an IL-17RA/IL-17RC complex and IL12RB1. Preferred combinations targeted by bispecific antibodies used in the present invention are: IL-17 and IL-23; IL-17 and IL-23p19; IL17RA and IL-23; and IL-17RA and IL-23p19. A particularly preferred bispecific antibody specifically binds to, and inhibits the activity of, each of IL-17 and IL-23p19.

Preferred IL-23 antagonists are antibodies that bind to, and inhibit the activity of, any of IL-23, IL-23p19, IL-12p40, IL23R, IL12RB1, and an IL-23R/IL12RB1 complex. Another preferred IL-23 antagonist is an IL-23 binding polypeptide which consists essentially of the extracellular domain of IL-23R, e.g., amino acids 1-353 of GenBankAAM44229, or a fragment thereof.

Antibody antagonists for use in the invention may be prepared by any method known in the art for preparing antibodies. The preparation of monoclonal, polyclonal, and humanized antibodies is described in Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378; Baca, et al. (1997) *J. Biol. Chem.* 272:10678-10684; Chothia, et al. (1989) *Nature* 342:877-883; Foote and Winter (1992) *J. Mol. Biol.* 224:487-499; and U.S. Pat. No. 6,329,511 issued to Vasquez, et at.

Any antigenic form of the desired target can be used to generate antibodies, which can be screened for those having the desired antagonizing activity. Thus, the eliciting antigen may be a peptide containing a single epitope or multiple epitopes, or it may be the entire protein alone or in combination with one or more immunogenicity enhancing agents known in the art. To improve the immunogenicity of an antigenic peptide, the peptide may be conjugated to a carrier protein. The antigen may also be an isolated full-length protein, a cell surface protein (e.g., immunizing with cells transfected with at least a portion of the antigen), or a soluble protein (e.g., immunizing with only the extracellular domain portion of the protein). The antigen may be expressed by a genetically modified cell, in which the DNA encoding the antigen is genomic or non-genomic (e.g., on a plasmid).

A peptide consisting essentially of a region of predicted high antigenicity can be used for antibody generation. For example, regions of high antigenicity of human p19 occur at amino acids 16-28; 57-87; 110-114; 136-154; and 182-186 of GenBank AAQ89442 (gi: 37183284) and regions of high antigenicity of human IL-23R occur at amino acids 22-33; 57-63; 68-74; 101-112; 117-133; 164-177; 244-264; 294-302; 315-326; 347-354; 444-473; 510-530; and 554-558 of GenBank AAM44229 (gi: 21239252), as determined by analysis with a Parker plot using Vector NTI® Suite (Informax, Inc, Bethesda, Md.).

Any suitable method of immunization can be used. Such methods can include use of adjuvants, other immunostimulants, repeated booster immunizations, and the use of one or more immunization routes. Immunization can also be performed by DNA vector immunization, see, e.g., Wang, et al. (1997) *Virology* 228:278-284. Alternatively, animals can be immunized with cells bearing the antigen of interest, which may provide superior antibody generation than immunization with purified antigen (Kaithamana, et al. (1999) *J. Immunol* 163:5157-5164).

Preferred antibody antagonists are monoclonal antibodies, which may be obtained by a variety of techniques familiar to skilled artisans. Methods for generating monoclonal antibodies are generally described in Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Typically, splenocytes isolated from an immunized mammalian host are immortalized, commonly by fusion with a myeloma cell to produce a hybridoma. See Kohler and Milstein (1976) *Eur. J. Immunol.* 6:511-519; Meyaard, et al. (1997) *Immunity* 7:283-290; Wright, et al. (2000) *Immunity* 13:233-242; Preston, et al. (1997) *Eur. J. Immunol.* 27:1911-1918. Alternative methods of immortalization include transformation with Epstein Barr Virus, oncogenes, or retroviruses, or other methods known in the art. See, e.g., Doyle, et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity, affinity and inhibiting activity using suitable binding and biological assays. For example, antibody to target binding properties can be measured, e.g., by surface plasmon resonance (Karlsson, et al. (1991) *J. Immunol. Methods* 145:229-240; Neri, et al. (1997) *Nat. Biotechnol.* 15:1271-1275; Jonsson, et al. (1991) *Biotechniques* 11:620-627) or by competition ELISA (Friguet, et al. (1985) *J. Immunol. Methods* 77:305-319; Hubble (1997) *Immunol. Today* 18:305-306).

Alternatively, one may isolate DNA sequences which encode a monoclonal antibody or a binding fragment thereof by screening a DNA library from human B cells, see e.g., Huse, et al. (1989) *Science* 246:1275-1281. Other suitable techniques involve screening phage antibody display libraries. See, e.g., Huse et al., *Science* 246:1275-1281 (1989); and Ward et al., *Nature* 341:544-546 (1989); Clackson et al. (1991) *Nature* 352: 624-628 and Marks et al. (1991) *J. Mol. Biol.* 222: 581-597; Presta (2005) *J. Allergy Clin. Immunol.* 116:731.

Preferred monoclonal antibodies for use in the present invention are "chimeric" antibodies (immunoglobulins) in which the variable domain is from the parental antibody generated in an experimental mammalian animal, such as a rat or mouse, and the constant domains are obtained from a human antibody, so that the resulting chimeric antibody will be less likely to elicit an adverse immune response in a human subject than the parental mammalian antibody. More preferably, a monoclonal antibody used in the present invention is a "humanized antibody", in which all or substantially all of the hypervariable loops (e.g., the complementarity determining regions or CDRs) in the variable domains correspond to those of a non-human immunoglobulin, and all or substantially all of the framework (FR) regions in the variable domains are those of a human immunoglobulin sequence. A particularly preferred monoclonal antibody for use in the present invention is a "fully human antibody", e.g., an antibody that comprises human immunoglobulin protein sequences only. A fully human antibody may contain carbohydrate chains from the cell species in which it is produced, e.g., if produced in a mouse, in a mouse cell, or in a hybridoma derived from a mouse cell, a fully human antibody will typically contain murine carbohydrate chains.

Monoclonal antibodies used in the present invention may also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079.

The antagonistic antibodies used in the present invention may have modified (or blocked) Fc regions to provide altered effector functions. See, e.g., U.S. Pat. No. 5,624,821; WO2003/086310; WO2005/120571; WO2006/0057702. Alterations of the Fc region include amino acid changes (substitutions, deletions and insertions), glycosylation or deglycosylation, and adding multiple Fc. Changes to the Fc can alter the half-life of therapeutic antibodies, enabling less frequent dosing and thus increased convenience and decreased use of material. See Presta (2005) *J. Allergy Clin. Immunol.* 116:731 at 734-35.

The antibodies may also be conjugated (e.g., covalently linked) to molecules that improve stability of the antibody during storage or increase the half-life of the antibody in vivo. Examples of molecules that increase the half-life are albumin (e.g., human serum albumin) and polyethylene glycol (PEG). Albumin-linked and PEGylated derivatives of antibodies can be prepared using techniques well known in the art. See, e.g., Chapman, A. P. (2002) *Adv. Drug Deliv. Rev.* 54:531-545; Anderson and Tomasi (1988) *J. Immunol. Methods* 109:37-42; Suzuki, et al. (1984) *Biochim. Biophys. Acta* 788:248-255; and Brekke and Sandlie (2003) *Nature Rev.* 2:52-62).

Bispecific antibodies that antagonize both IL-17 and IL-23 activity can be produced by any technique known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan, et al. (1985) *Science* 229: 81. These bifunctional antibodies can also be prepared by disulfide exchange, production of hybrid-hybridomas (quadromas), by transcription and translation to produce a single polypeptide chain embodying a bispecific antibody, or transcription and translation to produce more than one polypeptide chain that can associate covalently to produce a bispecific antibody. The contemplated bispecific antibody can also be made entirely by chemical synthesis. The bispecific antibody may comprise two different variable regions, two different constant regions, a variable region and a constant region, or other variations.

Antibodies used in the present invention will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-1}$ M, and most preferably at least $10^{-11}$ M (see, e.g., Presta, et al. (2001) *Thromb. Haemost.* 85:379-389; Yang, et al. (2001) *Crit. Rev. Oncol. Hematol.* 38:17-23; Carnahan, et al. (2003) *Clin. Cancer Res.* (Suppl.) 9:3982s-3990s).

IL-17 antagonists and IL-23 antagonists are typically administered to a patient as a pharmaceutical composition in which the antagonist is admixed with a pharmaceutically acceptable carrier or excipient, see, e.g., *Remington's Pharmaceutical Sciences and U.S. Pharmacopeia: National Formulary*, Mack Publishing Company, Easton, Pa. (1984). The pharmaceutical composition may be for ululated in any manner suitable for the intended route of administration. Examples of pharmaceutical formulations include lyophilized powders, slurries, aqueous solutions, suspensions and sustained release formulations (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

The route of administration will depend on the properties of the antagonist or other therapeutic agent used in the pharmaceutical composition. A possible administration route is to administer the pharmaceutical composition topically to the eye in the form of an ointment, gel or droppable liquids using an ocular delivery system known to the art such as an applicator or eyedropper. Alternatively, the pharmaceutical composition may be administered intraocularly via an polymer implant that is placed under the under the conjunctiva of the eye or through injection directly into the eye. Preferably, pharmaceutical compositions containing IL-17 antagonists and IL-23 antagonists are administered systemically by oral ingestion, injection or infusion by intravenous, intraperitoneal, intracerebral, intramuscular, intraocular, intraarterial, intracerebrospinal, intralesional, or pulmonary routes, or by sustained release systems such as implants. Injection of gene transfer vectors into the central nervous system has also been described (see, e.g., Cua, et al. (2001) *J. Immunol.* 166:602-608; Sidman et al. (1983) *Biopolymers* 22:547-556; Langer, et al. (1981) *J. Biomed. Mater. Res.* 15:167-277; Langer (1982) *Chem. Tech.* 12:98-105; Epstein, et al. (1985) *Proc. Natl. Acad. Sci. USA* 82:3688-3692; Hwang, et al. (1980) *Proc. Natl. Acad. Sci. USA* 77:4030-4034; U.S. Pat. Nos. 6,350,466 and 6,316,024).

The pharmaceutical compositions used in the invention may be administered according to any treatment regimen that ameliorates or prevents one or more symptoms of the AOID. Selecting the treatment regimen will depend on several composition-dependent and patient-dependent factors, including but not limited to the half-life of the antagonist, the severity of the patient's symptoms, and the type or length of any adverse effects. Preferably, an administration regimen maximizes the amount of therapeutic agent delivered to the patient consistent with an acceptable level of side effects. Guidance in selecting appropriate doses of therapeutic antibodies and small molecules is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Biological antagonists such as antibodies may be provided by continuous infusion, or by doses at intervals of, e.g., once per day, once per week, or 2 to 7 times per week, once every other week, or once per month. A total weekly dose for an antibody is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis. Determination of the appropriate dose is made by the clinician, e.g., using parameters or factors known or suspected in the art to affect treatment or predicted to affect treatment. Generally, the beginning dose is an amount somewhat less than the optimum dose and the dose is increased by small increments thereafter until the desired or optimum effect is achieved relative to any negative side effects.

Treatment regimens using IL-17 or IL-23 antagonists will typically be determined by the treating physician and will take into account the patient's age, medical history, disease symptoms, and tolerance for different types of medications and dosing regimens. Generally the treatment regimen is designed to suppress the overly aggressive immune system, allowing the body to eventually re-regulate itself, with the result often being that after the patient has been kept on systemic medications to suppress the inappropriate immune response for a finite length of time (for example, one year), medication can then be tapered and stopped without recurrence of the autoimmune attack. Sometimes resumption of the attack does occur, in which case the patient must be re-treated.

Thus, in some cases, the physician may prescribe the patient a certain number of doses of the antagonist to be taken over a prescribed time period, after which therapy with the antagonist is discontinued. Preferably, after an initial treatment period in which one or more of the acute symptoms of the disease disappear, the physician will continue the agonist therapy for some period of time, in which the amount and/or frequency of antagonist administered is gradually reduced before treatment is stopped.

The present invention also contemplates treatment regimens in which an IL-17 antagonist is used in combination with an IL-23 antagonist. Such regimens may be especially useful in treating the acute phase of AOID, in which the IL-17 antagonist inhibits the activity of existing $Th_{17}$ cells, while the IL-23 antagonist prevents the generation of new $Th_{17}$ cells. Such combination therapy may provide effective treatment of AOID using a lower dose of the IL-17 antagonist and/or administering the IL-17 antagonist for a shorter period of time. As symptoms ameliorate, therapy with IL-17 antagonist is preferably discontinued, while administration of the IL-23 antagonist is continued to prevent generation of new autoreactive $Th_{17}$ cells that could lead to recurrence of the disease. The two antagonists may be administered at the same time in a single composition, or in separate compositions. Alternately, the two antagonists may be administered at separate intervals. Different doses of the antagonists may also be used. Similarly, a bispecific antagonist may also be administered during the acute phase and gradually withdrawn, followed by treatment with an IL-23 antagonist to maintain repression of the disease.

The treatment regimen may also include use of other therapeutic agents, to ameliorate one or more symptoms of the AOID or to prevent or ameliorate adverse effects from the antagonist therapy. Examples of therapeutic agents that have been used to treat AOID symptoms are steroids and other anti-inflammatories. Examples of such therapies include, but are not limited to, steroids such as dexamethasone, fluorometholone, and prednisolone, as well as non-steroidal anti-inflammatories such as indomethacin, aspirin, flubiprofen and diclofenac, antimetabolites (e.g., methotrexate, azathioprine), inhibitors of transcription factors (e.g., cyclosporine, tacrolimus), and DNA cross-linking agents (e.g., cyclophosphamide, chlorambucil). New agents directed against cytokines and their receptors, many of which act by inhibiting important Th1 cytokine rather than signaling pathways, are beginning to be used for treatment of patients with uveitis. These include TNF inhibitors such as Infliximab (Remicade®, Centocor, Malvern, Pa.), Etanercept (Enbrel®, Amgen, Thousand Oaks, Calif.), and Adalimumab (Humira®, Abbott Laboratories, Abbott Park, Ill.) and specific inhibitors of IL-2 signaling, including Daclizumab (Zenapax®, Roche Laboratories, Nutley, N.J.) and Basiliximab (Simulect®, Novartis Pharmaceutical Co., East Hanover, N.J.).

In any of the therapies described herein in which two or more different therapeutic substances are used (e.g., an IL-17 antagonist and an IL-23 antagonist, or an IL-17 antagonist and a therapeutic agent that does not antagonize IL-17 or IL-23 activity), it will be understood that the different therapeutic substances are administered in association with each other, that is, they may be administered concurrently in the same pharmaceutical composition or as separate compositions or the substances may be administered at separate times, and in different orders.

Diagnosing the presence of an AOID in a patient will typically involve examining the patient for symptoms known to be consistent with such diseases. For example, the typical presentation of anterior uveitis involves pain, photophobia, and hyperlacrimation. Patients report a deep, dull, aching of the involved eye and surrounding orbit. Associated sensitivity to lights may be severe. Excessive tearing occurs secondary to increased neural stimulation of the lacrimal gland and the patient does not report a foreign-body sensation. Visual acuity is variable ranging from mild blur to significant vision loss if synechiae or cyclitic membranes are present. An examination may reveal mild to moderate lid swelling resulting in pseudoptosis. A deep, perilimbal injection of the conjunctiva and episclera is typical, although the palpebral conjunctiva is characteristically normal. The cornea may display mild edema.

The hallmark signs of anterior uveitis include cells and flare in the anterior chamber. If the anterior chamber reaction is significant, small gray to brown endothelial deposits known as keratic precipitates may be present. This can then lead to endothelial cell dysfunction and corneal edema. Iris findings may include adhesions to the lens capsule (posterior synechiae) or, less commonly, to the peripheral cornea (anterior synechiae). Additionally, granulomatous nodules may appear on the surface of the iris. Intraocular pressure (IOP) is initially reduced in the involved eye due to secretory hypotony of the ciliary body. However, as the reaction persists, inflammatory by-products may accumulate in the trabeculum. If this debris builds significantly, and if the ciliary body resumes its normal secretory output, IOP can rise sharply resulting in a secondary uveitic glaucoma.

Identifying patients who are susceptible for an AOID will typically taking a personal and family medical history, and may include genetic testing. For example, some individuals will have genetic predisposition to uveitis which is related to autoimmune disease processes. The most common of these susceptibility genes is the HLA B27 haplotype, which can predispose to uveitis alone or also to the Seronegative Spondyloarthropathies and the enteropathic arthropathies. Examples are ankylosing spondylitis, reactive arthritis (Reiters syndrome), psoriatic arthritis, irritable bowel disease and Crohn's disease. A patient may also be diagnosed as susceptible for an AGED if there was a family history of any of these autoimmune diseases, or the patient has already been diagnosed with such a disease.

The effectiveness of the antagonist therapy for preventing or treating AOID in a particular patient can be determined using diagnostic measures such as reduction or occurrence of inflammatory symptoms of, e.g., the amount of ocular inflammation or level of inflammatory cytokines in the affected eye(s). The symptoms of ocular inflammation for the most part depend on the affected area of the eye. Most common signs and symptoms are: pain redness, floaters, decreased vision, and light sensitivity. The level of inflammatory cytokines can be measured, e.g, by contacting a binding compound for the inflammatory cytokine of interest with a sample from the patient's eye as well as with a sample from a control subject or from unaffected tissue or fluid from the patient, and then comparing the cytokine levels detected by the binding compound. Expression or activity from a control subject or control sample can be provided as a predetermined value, e.g., acquired from a statistically appropriate group of control subjects.

Examples

The present invention is based upon studies in IL-23p19 knockout (KO) mice and administration of anti-IL-23p19 and anti-IL17 antibodies to murine models of autoimmune uveitis. These experiments were performed according to the Materials and Methods described in Section II below.

I. Results and Discussion

In the experiments involving IL-23p19 KO mice, the EAU susceptibility of IL-23p19 KO (IL-23 deficient) mice were compared to the EAU susceptibility of IL-12p35 KO (IL-12 deficient) and IL-12p40 KO (IL-12 and IL-23 deficient) mice. All mice were on the C57BL/6 background and the EAU induction and scoring was as described in General Methods below. It was found that IL-12p35 is not required for generation of IRBP-specific eye tissue destruction. In contrast, IL-23p19 is essential for development of EAU (Table 1). Cytokine analysis of lymph node cell cultures derived from IRBP-immunized mice showed that the EAU susceptible IL-12 deficient mice (IL-12p35KO) had elevated levels of IFN-γ, IL-6, IL-17 and IL-18, compared to IL-23 deficient mice (IL-23p19KO and IL-12p40KO). Delayed hypersensitivity (DTH) responses to IRBP of the 3 KO strains, examined by the ear swelling assay, showed that DTH response to IRBP was well correlated with the EAU scores or the respective mice, with significantly lower responses for p19 and p40 KO and significantly higher responses in p35 KO compared to wild-type (WT).

TABLE 1

IL-23, but not IL-12, is essential for EAU development.

| | EAU Average score +/− SE | DTH Specific swelling +/− SE (μm × 10−1) | IFN-γ (ng/ml) | IL-6 (ng/ml) | IL-17 (ng/ml) | IL-18 (ng/ml) |
| --- | --- | --- | --- | --- | --- | --- |
| Wild type | 0.21 ± 0.11 | 44 ± 7 | 39 | 3.2 | 2.2 | 0.25 |
| IL-12p35KO | 0.57 ± 0.12 | 57 ± 2 | 16 | 1.9 | 4.9 | 0.29 |
| IL-23p19KO | 0 | 25 ± 4 | 6.5 | 0.55 | 1.2 | 0.10 |
| IL-12p40KO | 0 | 22 ± 3 | <1 | .08 | 0.85 | 0.11 |

These results were further supported by experiments using an anti-mouse IL-23p19 antibody in a mouse model of uveitis, in the highly susceptible B10.RIII strain. It was found that anti-mouse IL-23p19 antibody treatment significantly blocked immune-mediated eye inflammation. At the dose of 330 μg per mouse every other day, the EAU disease index of anti-IL-23p19 treated mice was dramatically reduced compared to anti-isotype antibody treated and no antibody controls as determined by histopathology of eyes collected on day 11 after immunization (Table 2). In addition, anti-IL-23p19 therapy was as efficacious as Prednisone in blocking EAU. The expression levels of IL-17, but not IFN-γ mRNA in the eyes of anti-IL-23p19 treated mice were lower than the control groups suggesting that targeting IL-23 inhibited EAU by blocking infiltration of IL-17 producing cells or preventing the expansion of the pathogenic IL-17 producing cells within the eyes. Neutrophil elastase and myeloperoxidase mRNA levels of anti-IL-23p19 treated mice were comparable to naïve as well as Prednisone control groups, whereas the "No antibody" and isotype control treated mice exhibited 10- to 100-fold increase in expression of these inflammatory genes. Other proinflammatory factors such as IL-1β, TNF, IL-6, NOS2 and COX2 were somewhat reduced in anti-IL-23p19 treated mice. These results demonstrate that targeting IL-23 inhibits the development of autoimmune uveitis.

A second part of this experiment examined the stage of the pathogenic process during which IL-23 was required. Mice were treated with 500 μg of anti-IL-23 p19 antibody every other day starting 7 days after immunization and the disease was compared to mice that were treated from day before immunization (as above). EAU could be prevented by early treatment with either anti-p19 or anti-p40 antibodies. However, when treatment was started 7 days after immunization, a time point when uveitogenic effector T cells have already

TABLE 2

Anti-IL-23p19 treatment inhibits EAU and expression of inflammatory cytokines in the eye.

| | Histopathology 0 = normal 1 = few monocyte infiltration 4 = severe damage (individual eyes) | Eye Quantitative-PCR gene expression analysis (Shown as expression relative to Ubiquitin). Tissue samples collected on day 11 after IRBP immunization. | | | | | | | | |
|---|---|---|---|---|---|---|---|---|---|---|
| | | IFN-γ | IL-6 | IL-17 | TNF | IL-1β | NOS2 | COX2 | Neutrophil Elastase | Myeloper- oxidase |
| Naïve mice | 0 0 0 0 0 | 0.44 | 0.16 | 0 | 0 | 3.8 | 2.7 | 4.8 | 0.1 | 0 |
| No mAb control | 4 4 4 4 4 3 3 3 2 2 2 2 1 1 1 1 1 1 1 1 | 6.2 | 37.6 | 7.1 | 37.8 | 117.8 | 22.2 | 24.6 | 1.23 | 4.11 |
| Isotype mAb control | 4 4 4 4 4 4 2 1 1 1 1 1 1 1 1 1 1 1 1 0 | NA | 13.6 | 3.1 | 28.3 | 103.0 | 19.2 | 14.5 | 1.35 | 3.09 |
| Anti- IL- 23p19 | 1 1 1 1 1 1 1 1 1 1 1 1 1 0 0 0 0 0 | 6.9 | 10.3 | .013 | 12.5 | 64.3 | 14.7 | 8.9 | 0.08 | 0 |
| Prednisone | 4 4 2 1 1 1 1 1 1 0 0 0 0 0 0 0 | 0.51 | 1.2 | 0 | 17.9 | 74.6 | 5.2 | 14.6 | 0.55 | 0 |

Another set of experiments comparing treatment with anti-IL-23p19 antibodies to treatment with anti-IL-12p40 antibodies was also performed. In this experiment mice received 500 μg of the indicated antibodies every other day, starting the day before immunization, and the eyes and lymphoid organs were collected 17 days after immunization, or 6-7 days after disease onset in controls. The data indicated that anti-IL-23p19 antibodies were as effective as anti-p40 antibodies at blocking the onset of uveitis. The data are shown in Table 3.

In addition, cytokine protein expression in the lymph nodes of these mice was assessed by multiplex ELISA. These data show that treatment with IL-23 antagonists lessens the production of Th1 and pro-inflammatory cytokines. The data are shown in Table 3.

been primed and can be isolated from the LN and spleen, EAU development could not be aborted and the disease scores developed by treated mice were similar to control. This suggests that the requirement for IL-23 occurs at an early stage of disease pathogenesis. The data are shown in Table 4.

TABLE 4

Treatment with anti-p19 antibody prevents, but does not reverse, EAU.

| Start of treatment | Antibody | EAU score ± SE |
|---|---|---|
| day-1 | Anti-isotype | 2.9 ± 0.1 |
| | Anti P19 | 0.6 ± 0.6 |
| | Anti P40 | 0 ± 0 |

TABLE 3

Anti-IL-23p19 treatment inhibits EAU and systemic cytokine responses to the uveitis antigen.

| Sample | EAU score of individual eyes | IL-2 pg/ml | IL-4 pg/ml | IL-5 pg/ml | IL-6 pg/ml | IL-10 pg/ml | IFN-γ pg/ml | TNF-α pg/ml | IL-12 pg/ml | IL-17 pg/ml |
|---|---|---|---|---|---|---|---|---|---|---|
| Control | 3, 3, 3, 3, 3, 3, 3, 3, 0, 0.25 | 247.6 | 0.4 | <3.1 | 145.7 | 8.6 | 1295.3 | 46.5 | 2.7 | 72.9 |
| Anti IL-23p19 | 3, 3, 0, 0, 0, 0, 0, 0, 0, 0 | 115.0 | 1.3 | 19.1 | 163.7 | 5.5 | 1453.3 | 87.5 | 2.1 | 37.0 |
| Anti Isotype | 3, 3, 3, 3, 3, 3, 3, 3, 3, 3 | 205.2 | 1.4 | <3.1 | 206.7 | 12.4 | 2759.6 | 51.2 | 3.1 | 198.0 |
| Anti IL-12p40 | 0.25, 0, 0, 0, 0, 0, 0, 0, 0, 0 | 101.9 | 0.4 | <3.1 | 26.5 | 4.4 | 305.5 | 16.6 | <0.8 | 29.7 |

TABLE 4-continued

Treatment with anti-p19 antibody prevents, but does not reverse, EAU.

| Start of treatment | Antibody | EAU score ± SE |
|---|---|---|
| day 7 | Anti-isotype | 2.05 ± 0.5 |
|  | Anti P19 | 2.35 ± 0.5 |
|  | Anti P40 | 2.075 ± 0.5 |

In the aggregate, these experiments demonstrate that neutralization of IL-23 prevents, but does not reverse, uveitis in animal models, and indicate that treatment with IL-23 antagonists should have a beneficial effect in chronic uveitis in humans by preventing recruitment of new T cells into the effector pool, thereby reducing the severity and halting progression of the disease.

To test whether IL-17 deficiency can affect EAU development, IL-17A$^{-/-}$ mice (see, e.g., Nakae et al. (2002) *Immunity* 17:375-387) were immunized with a uveitogenic regimen of IRBP. Inhibition or EAU by genetic IL-17 deficiency was only partial (Table 5). The relatively modest reduction of EAU scores in IL-17$^{-/-}$ mice might be explained by the fact that these mice are deficient for the IL-17A isoform of the cytokine, and under conditions of congenital deficiency might compensate with the usually less abundantly produced IL-17F isoform.

TABLE 5

Genetic IL-17 deficiency reduces, but does not abrogate, EAU susceptibility.

| Expt # | WT | IL-17A-/- |
|---|---|---|
| 1 | 0.5* | 0.5 |
|  | 1.5 | 1.0 |
|  | 0.8 | 0.9 |
|  | 0.8 | 0.1 |
|  | 0.4 | 0.9 |
|  | 1.3 | 0.6 |
|  |  | 0.5 |
| 2 | 0.5 | 0.5 |
|  | 0.9 | 0.0 |
|  | 1.8 | 0.3 |
|  | 1.0 | 0.0 |
|  | 1.5 |  |
|  | 0.5 |  |
| Average Score ± SE | 0.9 ± 0.1 | 0.5 ± 0.1 |

In contrast, neutralization of IL-17A with IL-17A antibodies in wild type mice, either through the entire course of disease or through the effector phase only (starting day 7), was protective. Importantly, unlike IL-23 neutralization, neutralization of IL-17 could inhibit disease when administered starting day 7 post immunization, when uveitogenic effectors have already been generated. Reduction in EAU scores correlated with reduction in the associated immunological responses, delayed-type hypersensitivity (DTH) and antigen specific LN cell proliferation. Thus, IL-17 has a role in the pathogenesis of EAU, and unlike IL-23, appears to participate in the effector phase of the disease. The data are shown in Table 6.

TABLE 6

Treatment with anti-IL-17A antibodies prevents and reverses EAU

| Start of treatment | Antibody | EAU score ± SE | DTH ± SE | Proliferation ± SE (×10$^{-3}$) |
|---|---|---|---|---|
| day-1 | Anti-isotype | 1.6 ± 0.7 | 16 ± 1 | 19.2 ± 1.2 |
|  | Anti IL-17 | 0.025 ± 0.025 | 7.6 ± 2 | 6.6 ± 6.4 |
| day 7 | Anti-isotype | 1.6 ± 0.6 | 20.2 ± 3 | 25.4 ± 1.4 |
|  | Anti IL-17 | 0.5 ± 0.5 | 6.0 ± 2 | 5.9 ± 0.3 |

Section II. Materials and Methods.

A. General

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001)*Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John. Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Cohowl, et al. (2001) *Current Protocols in Immunology*, Vol. 4, John Wiley, Inc., New York).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin. Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

B. Animals

IL-23 KO (p19 KO) was described in Cua, et al. (2003) *Nature* 421:744-748. IL-17$^{-/-}$ mice were produced as described in Nakae, et al. (2002) *Immunity* 17:375-387. IL-12p35 KO (P35 KO), IL-12p40 KO (P40 KO), IFN-γ KO (GKO) (all on C57BL/6 background) and C57BL/6 and BIOME, mice were purchased from Jackson Laboratories. Animals were kept in a specific pathogen-free facility and given water and standard laboratory chow ad libitum. Animal care and use were in compliance with institutional guidelines and with the Association for Research in Vision and Ophthalmology Statement for the Use of Animals in Ophthalmic and Vision Research.

C. EAU Induction and Scoring

CFA was purchased from Sigma. *Mycobacterium Tuberculosis* strain H37RA was purchased from Thomas Scientific. Purified *Bordetella* PT was purchased from Sigma-Aldrich. IRBP was isolated from bovine retinas, as described previously, using Con A-Sepharose affinity chromatography and fast performance liquid chromatography (see, e.g., Pepperberg et al. (1991) *Photochem Photobiol* 54:1057-1060). IRBP preparations were aliquoted and stored at −70° C. Human IRBP-derived peptide 161-180 (Karabezekian, Z. et al., (2005) *Invest Ophthalmol Vis Sci.* 46(10):3769-76) was synthesized by Fmoc chemistry (model 432A peptide synthesizer; Applied Biosystems, Foster City, Calif.).

Neutralizing anti-mouse IL-23 and anti-mouse IL-17A antibodies were provided by Schering-Plough Biopharma (Palo Alto, Calif.). Anti-mouse IL-23 was described previously (see, e.g., Langrish et al. (2005) *J Exp Med* 201:233-240). The C17.8 (anti-IL-12p40, rat IgG2a) hybridoma was provided by the Wistar Institute, Philadelphia, Pa. Monoclonal antibody was produced in ascites and purified by ion exchange HPLC by Harlan Bioproducts for Science (Indianapolis, Ind.). FITC-labeled anti-mouse CD4 (clone-L3T4), PE-labeled anti-mouse IL-17 (clone-TC11-18H10) and APC-labeled anti-IFN-γ (clone-XMG1.2) and cytokine secretion blacker (GolgiStop™) were purchased from Becton Dickinson (San Diego, Calif.). PMA, Ionomycin were purchased from LC Laboratories (Boston, Mass.).

EAU was induced by active immunization with 150 μg of IRBP for C57BL/6 mice and with 7 μg IRBP peptide 161-180 for B10RIII mice (Jackson Labs, Maine). For C57BL/6 mice, *Bordetella pertussis* toxin (0.5 μg/mouse) in PBS containing 2% normal mouse serum was given by intraperitoneal injection concurrently with immunization and in some experiments the IRBP was spiked with 500 μg of IRBP peptide 1-20 (Avichezer, D. et al. (2000), *Invest Ophthalmol Vis Sci.* 41(1): 127-31) to enhance the usually modest disease scores seen in this strain. Antigen solution was emulsified 1:1 v/v in CFA that had been supplemented with *Mycobacterium tuberculosis* strain H37RA to 2.5 mg/ml. A total of 200 μl of emulsion was injected s.c., divided into 3 sites (base of the tail and both thighs).

Alternatively, EAU was induced by adoptive transfer of a uveitogenic T cell line (see below). 1-2 million cells, freshly stimulated with antigen, were injected intraperitoneally. Clinical EAU was evaluated by fundoscopy under a binocular microscope after dilation of the pupil and was graded on a scale of 0-4 using criteria based on the extent of inflammatory lesions, as described in detail elsewhere (see, e.g., Agarwal and Caspi, (2004) *Methods Mol Med* 102:395-419; and Chan et al. (1990) *J Autoimmun* 3:247-255). Eyes harvested 17-21 days after immunization, or 14 days after adoptive transfer, were prefixed in 4% phosphate-buffered glutaraldehyde for 1 h (to prevent artifactual detachment of the retina) and then transferred to 10% phosphate-buffered formaldehyde until processing. Fixed and dehydrated tissue was embedded in methacrylate, and 4- to 6-μm sections were stained with standard H&E. Eye sections cut through pupillary-optic nerve planes were scored in a masked fashion. Severity of EAU was graded on a scale of 0-4 in half-point increments using the criteria described previously, based on the type, number, and size of lesions (see, Agarwal and Caspi, supra; and Chan et al. supra).

D. Determination of Immunological Responses

Delayed Type Hypersensitivity (DTH) to IRBP was evaluated by the ear swelling assay (see, e.g., Tarrant et al. (1998) *J Immunol* 161:122-127). For Ag-specific lymphocyte proliferation and cytokine production in primary cultures, the spleen and draining lymph nodes (inguinal and iliac) (5 per group) were collected at the end of each experiment as indicated. Lymphoid cells were pooled within the group, and were incubated with graded doses of Ag in triplicate 0.2-ml cultures, essentially as described (see, e.g., Avichezer et al. (2000) *Invest Ophthalmol Vis Sci.* 41:127-131). Proliferation was determined by [$^3$H]thymidine uptake. Cytokines were quantitated in 48-h Ag-stimulated supernatants using the Pierce Multiplex SearchLight Arrays technology (see, e.g., Moody et al. (2001) *Biotechniques* 31:186-190, 192-184).

E. Neutralization of IL-23, IL-12p40, and IL-17

B10RIII mice were immunized with IRBP or IRBP uveitogenic peptide (161-180) as indicated. Mice were injected intraperitoneally with 0.5 mg per dose of anti-p19, anti-p40, or anti-IL-17. Treatment was given every other day starting on day −1 through day 15 after immunization, covering both priming and effector phase (prevention protocol) or starting day 7 through day 15, covering the effector phase only (treatment). Controls were given the same regimen of isotype (rat IgG1). Eyes and lymphoid organs were harvested on day 17, 6-7 days after disease onset.

F. Uveitogenic T Cell Line

The uveitogenic Th1 cell line specific to a peptide of human IRBP (p16-180) has been described (see, e.g., Silver et al. (1995) *Invest Ophthalmol Vis Sci* 36:946-954). Briefly, the line was derived from draining lymph nodes of B10.RIII mice immunized with human IRBP peptide 161-180, polarized in vitro toward the Th1 phenotype by culture in the presence of antigen, IL-12, and anti-IL-4. Thereafter the cells were maintained by alternating cycles of expansion in IL-2 and restimulation with 1 μg/ml of p161-180 every 2 to 3 weeks in the presence of syngeneic splenocytes, irradiated with 3000 rads, as APCs. For EAU induction, cells freshly stimulated with Ag for 48 h were injected i.p. into naive syngeneic recipients.

G. Detection of Intracellular IL-17 and IFNγ

Short stimulation: T cell line was stimulated with 1 μg/ml IRBP peptide 161-180 in the presence of irradiated APCs for 24 h with the addition of GolgiStop™ protein transfer inhibitor (BD Biosciences, San Jose, Calif.) at the last 4 h. Thereafter, cells were separated on Ficoll, washed and stained for extracellular CD4. Than cells were washed, fixed, permeabilized with Cytofix/Cytoperm™ fixation and permeabilization buffer (BD Biosciences) and stained with PE-conjugated anti Il-17 and APC-conjugated anti IFN-γ for FACS analysis.

Long stimulation: T cell line was stimulated for 5 days with antigen (1 µg/ml IRBP peptide 161-180) or antigen+rIL-23 (10 ng/ml) or antigen+IL-23+anti IFN-γ (10 µg/ml) in the presence of irradiated APCs. During the last 4 h of incubation cells were stimulated with PMA and Ionomycin with the addition of GolgiStop™ protein transfer inhibitor (BD Biosciences). Thereafter cells were treated and stained for intracellular IL-17 and IFN-γ as mentioned above.

H. IL-17 and IFNγ Assays

After 48 h of stimulation with 1 µg/ml IRBP peptide 161-180 in the presence of irradiated APCs the T cell line was adoptively transferred ($2\times10^6$/mouse) i.v. to naïve Thy1.1/0.2 heterozygous mice. Ninety h later spleens were harvested and splenocytes were stimulated with IRBP peptide 161-180 for 24 h with the presence of PMA, ionomycin and GolgiStop™ protein transfer inhibitor (BD Biosciences) at the last 4 h. Thereafter cells were treated and stained for intracellular IL-17 and IFN-γ as mentioned above.

I. Statistical Analysis

Experiments were repeated at least twice, and usually three or more times. Tables show data compiled from a representative experiment. Statistical analysis of EAU scores, was by Snedecor and Cochran's test for linear trend in proportions (nonparametric, frequency-based) (see, e.g., Snedecor and Cochran (1967) *Statistical Methods Iowa State University Press*, Ames, Iowa: p. 248). Each mouse (average of both eyes) was treated as one statistical event. DTH and proliferation were examined by t-test (2 tailed). Cytokine responses were assayed on pooled samples (usually 5 mice per group).

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

All citations herein are incorporated herein by reference to the same extent as if each individual publication or patent document was specifically and individually indicated to be incorporated by reference. However, citation herein of any publication or patent document is not intended as an admission that the cited reference is pertinent prior art, nor does it constitute any admission as to the contents or effective prior art date of the reference.

What is claimed is:

1. A method of treating an autoimmune-mediated ocular inflammatory disease (AOID) comprising administering to a subject in need of such treatment an antagonist of interleukin-23 (IL-23), wherein the AOID is chronic uveitis and the antagonist is a monoclonal antibody that specifically binds to the p19 subunit of IL-23.

\* \* \* \* \*